United States Patent [19]

Beplate

[11] Patent Number: 5,575,279
[45] Date of Patent: Nov. 19, 1996

[54] DUAL-FILTERED ROTARY ISOLATION VALVE FOR RESUSCIATION

[75] Inventor: Douglas K. Beplate, Washington, Utah

[73] Assignee: Emergency Filtration Products, Inc., St. George, Utah

[21] Appl. No.: 587,805

[22] Filed: Jan. 2, 1996

[51] Int. Cl.[6] .................................................. A61M 16/00
[52] U.S. Cl. ................................ 128/203.11; 128/202.28; 128/202.29
[58] Field of Search ..................... 128/202.28, 202.29, 128/203.11

[56] References Cited

U.S. PATENT DOCUMENTS

| | | | |
|---|---|---|---|
| 3,018,775 | 1/1962 | Wilson et al. | 128/203.11 |
| 3,099,985 | 8/1963 | Wilson et al. | 128/203.11 |
| 4,811,730 | 3/1989 | Milano | 128/203.11 |
| 4,909,245 | 3/1990 | Wollenhaupt | 128/203.11 |
| 5,005,568 | 4/1991 | Loescher et al. | 128/202.28 |
| 5,230,330 | 7/1993 | Price | 128/203.11 |

Primary Examiner—Aaron J. Lewis
Attorney, Agent, or Firm—Thompson E. Fehr

[57] ABSTRACT

An isolation valve for the resuscitation of patients which has an upper housing and a lower housing that snap together, rotate with respect to one another, and utilize a flexible diaphragm which extends into the small space between the upper housing and the lower housing to assure the establishment of an air-tight seal between the upper housing and the lower housing. The upper housing begins with an upper tube that expands outward to create an upper chamber segment. The lower housing has a lower chamber segment, the wall of which lower chamber segment establishing the snap-fit with the wall of the upper chamber segment. The lower chamber segment is formed by the outward expansion of a lower tube. Breath exhaled by a care provider proceeds along the upper tube to the upper chamber segment where it must pass through an upper filter segment, a lower filter segment, and a space between the two that provides a volume to retain any moisture which evades the filter segments. The exhaled breath from the care provider then passes through a check valve that precludes exhaled breath from the patient from traveling to the care provider and then into the lower tube. Breath exhaled by the patient is exhausted to the atmosphere through one or more apertures in the bottom of the lower chamber segment after having passed through an exhalation filter.

12 Claims, 3 Drawing Sheets

DUAL-FILTERED ROTARY ISOLATION VALVE FOR RESUSCITATION

BACKGROUND OF THE INVENTION

1. Field of the Invention

This invention relates to a valve which isolates a patient from a provider of care when such provider of care attempts to resuscitate such patient by forcing the provider's breath into the patient's lungs.

2. Description of the Related Art

A variety of United States and foreign patents have been issued for devices which provide some degree of isolation between a patient and a care provider who is attempting to resuscitate the patient.

These include the following U.S. Pat. Nos. 3,158,152; 3,242,921; 3,923,054; 4,520,811; 4,811,730; 4,998,530; 5,005,568; 5,020,529; 5,146,914; 5,295,478; and 5,357,951. Similar foreign patents are the following: German (DDR) patent no. 53 856, German (FDR) patent no. 2 203 850, and French patent no. 2 664 167.

But none of these prior patents provides filters for all pathways that may be taken by breath exhaled by the care provider and the patient while having a path that would enable the often weak incipient breath of a patient to escape from the patient's lungs to the atmosphere even if the care provider is exhaling at the same time. Moreover, none of these prior patents provides an air-tight seal while allowing rotation between the portion of the valve to which a mouthpiece may be attached for the care provider and the portion of the valve to which a mask or a mouthpiece may be attached for the patient—a movement essential for maximizing comfort for both patient and care provider during often lengthy attempts at resuscitation. Increased comfort for the care provider will usually translate into both a longer period during which resuscitation may be attempted and greater alertness of the care provider during this period. Finally, none of the prior patents provides two filter segments in the most direct pathway between the patient and the care provider to minimize the possibility of fluid passing between the care provider and the patient while also establishing a space between such filter segments which is large enough to accommodate any fluid that manages to evade one of the filter segments without significantly obstructing the flow of breath from the care provider.

SUMMARY OF THE INVENTION

As its name implies, the Dual-filtered Rotary Isolation Valve for Resuscitation filters both the air exhaled by the provider of care and the air exhaled by the patient. Moreover, the path of exhaust air from the patient is not required to lift any physical object before reaching the atmosphere; so, small, incipient breaths by a patient who had previously ceased breathing will not be retarded. Similarly, the usually stronger breath of the care provider does not act to close any aperture through which the patient's breath reaches the atmosphere, even if both the provider of care and the patient breathe simultaneously.

To achieve low production costs and to minimize any slight potential for failure, the Dual-filtered Rotary Isolation Valve for Resuscitation has an extremely simple construction. There is an upper housing and a lower housing which snap together to permit rotation to achieve the most comfortable and efficient orientation of the upper housing with respect to the provider of care while simultaneously creating the most comfortable and efficient orientation of the lower housing with respect to the patient. Of course, the upper housing is directed toward the care provider; and the lower housing is directed toward the patient. Preferably, the provider of care will utilize a mouthpiece that may be attached to the upper housing while a mask may be connected to the lower housing for the patient.

There are only three other basic components: (a) a flexible diaphragm which includes a check valve, preferably a duckbill valve, for precluding the exhaled breath of the patient from proceeding through the upper housing to the care provider and which, to form an air-tight seal between the overlapping portions of the upper housing and the lower housing (which overlapping portions necessarily have some space between each other to effect the desired rotatability of the upper housing with respect to the lower housing) through which the unfiltered breath of the patient cannot pass, extends into the space between the overlapping portions of the upper housing and the lower housing; (b) a transmission filter; and (c) an exhalation filter.

The primary purpose of both the transmission filter and the exhalation filter is to prevent contaminants associated with bodily fluids of either the care provider or the patient from reaching the other person, i.e., either the care provider or the patient.

Since the most direct potential route for any such cross-contamination is directly between the upper housing and the lower housing, the transmission filter intercepts this route. Because the check valve precludes the exhaled breath of the patient from proceeding through the upper housing to the care provider, the preferred construction of the transmission filter minimizes the possibility of fluids passing from the care provider to the patient, although it also impedes the movement of fluids in any breath from the patient that may manage to pass the check valve. The transmission filter is constructed with an upper filter segment, which is on the side of the transmission filter that is upstream with respect to air coming from the care provider, and a lower filter segment, which is on the side of the transmission filter that is downstream with respect to air coming from the care provider. Preferably, the upper filter segment is hydrophobic to repel any moisture in the breath from the care provider. To create a volume where any fluids that manage to evade the upper filter segment may accumulate without significantly obstructing the flow of the care provider's breath, a ring spacer attaches on one side to the upper filter segment and on its opposite side to the lower filter segment. (The center of the ring spacer is hollow to create the desired volume.) To absorb fluids which do enter the volume inside the ring spacer, the lower filter segment will be hydrophilic

DESCRIPTION OF THE PREFERRED EMBODIMENT

Figure 1:
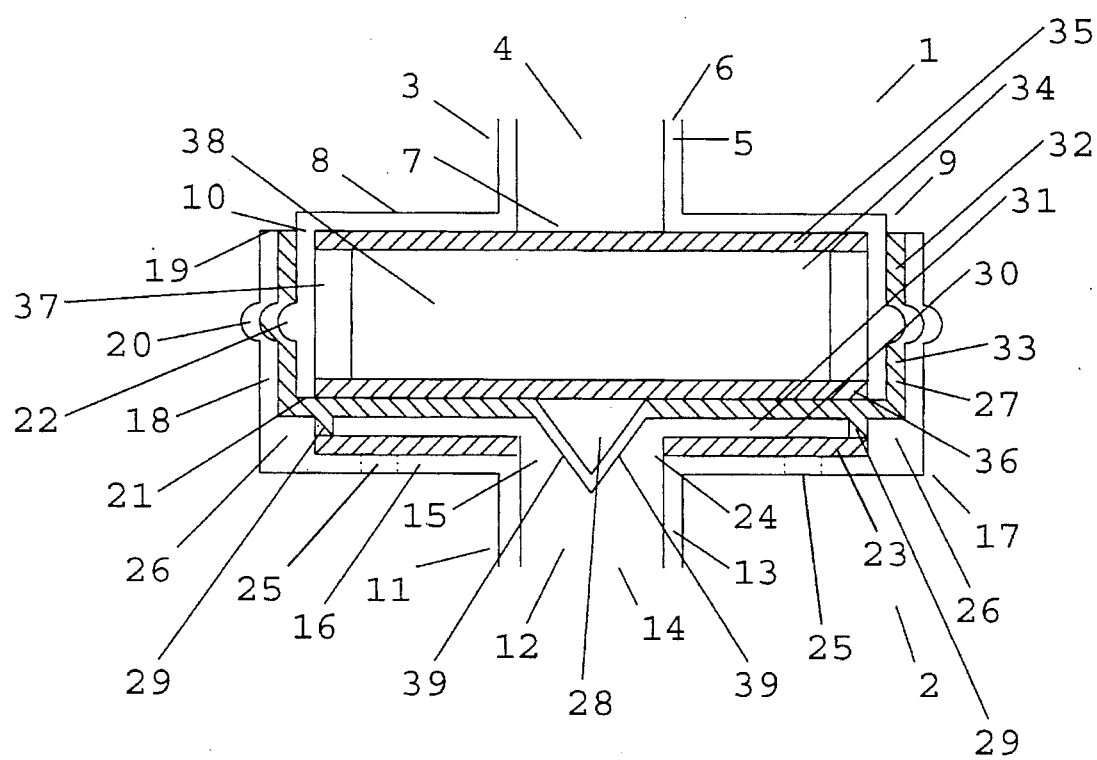
FIG. 1 illustrates the Dual-filtered Rotary Isolation Valve with the valve lips closed.

The Dual-filtered Rotary Isolation Valve for Resuscitation, as illustrated in FIG. 1, has an upper housing 1 and a lower housing 2.

The upper housing 1 is a unitary piece having an upper tube 3 with a bore 4 formed by the surrounding upper tube wall 5. The first end 6 of the upper tube 3 may go directly into the care provider's mouth (not shown) or, preferably, is connected to a mouthpiece (not shown) to be placed into the mouth of the care provider. At the second end 7 of the upper tube 3, the upper tube wall 5 expands outward to create the top 8 of an upper chamber segment 9 and then returns to its original direction to form the wall 10 of the upper chamber segment 9. The cross sections of the upper tube 3 and of the upper chamber segment 9 are both circular and are concentric with one another.

The lower housing 2 is a unitary piece having an lower tube 11 with a bore 12 formed by the surrounding lower tube wall 13. The first end 14 of the lower tube 11 may go directly into the patient's mouth (not shown) or, preferably, is connected to a mask (not shown) to be placed around the nose and mouth of the patient, or a mouthpiece (not shown) to be placed into the mouth of the patient. At the second end 15 of the lower tube 11, the lower tube wall 13 expands outward to create the bottom 16 of a lower chamber segment 17 and then returns to its original direction to form the wall 18 of the lower chamber segment 17. The cross sections of the lower tube 11 and of the lower chamber segment 17 are both circular and are concentric with one another.

The inner diameter of the wall 18 of the lower chamber segment 17 is slightly greater than the outer diameter of the wall 10 of the upper chamber segment 9 to permit the lower chamber segment 17 to rotate with respect to the upper chamber segment 9. Additionally, at a location between the bottom 16 of the lower chamber segment 17 and the top 19 of the wall 18 of the lower chamber segment 17, the wall 18 of the lower chamber segment 17 bulges outward to create an annular channel 20. Similarly, at a location between the top 8 of the upper chamber segment 9 and the bottom 21 of the wall 10 of the upper chamber segment 9 aligned with the annular channel 20 in the wall 18 of the lower chamber segment 17, the wall 10 of the upper chamber segment 9, protrudes outward to create an annular ridge 22 which fits within the annular channel 20 so that the lower chamber segment 17 can be snap-fit onto the upper chamber segment 9. Again, however, to permit rotation of the upper chamber segment 9 with respect to the lower chamber segment 17, the inner diameter of the annular channel 20 is slightly greater than the outer diameter of the annular ridge 22.

An exhalation filter 23 is placed on the bottom 16 of the lower chamber segment 17. The exhalation filter 23 contains an aperture 24 which, preferably, aligns with the bore 12 of the lower tube 11. One and, preferably, more apertures 25 also exist in the bottom 16 of the lower chamber segment 17.

At the junction of the bottom 16 of the lower chamber segment 17 and the wall 18 of the lower chamber segment 17 is formed an annular step 26. A flexible diaphragm 27 having a check valve 28 near the center of the flexible diaphragm 27 has a support 29 which rests on the exhalation filter 23 adjacent to the support 29 but covers only the outer edge of the exhalation filter 23 so that the majority of the surface 30 of the exhalation filter 23 that is opposite to the bottom 16 of the lower chamber segment 17 is adjacent to a passage 31 which communicates with the bore 12 of the lower tube 11.

The outer edge 32 of the flexible diaphragm 27 extends into the space 33 between the wall 18 of the lower chamber segment 17 and the wall 10 of the upper chamber segment 9. Moreover, the bottom 21 of the wall 10 of the upper chamber segment 9 rests on the diaphragm 27. Thus, the diaphragm 27 forms an air-tight seal between the upper chamber segment 9 and the lower chamber segment 17.

Filling the upper chamber segment 9 and adjacent to the diaphragm 27 is the transmission filter 34.

The transmission filter 34 has an upper filter segment 35 and a lower filter segment 36. The upper filter segment 35 is adjacent to the top 8 of the upper chamber segment 9; the lower filter segment 36 is adjacent to the diaphragm 27. An annular spacer 37 separates the upper filter segment 35 from the lower filter segment 36 and thereby creates air space 38.

When the care provider exhales into the upper tube 3, the breath of the care provider passes through the bore 4 of the upper tube 3, through the upper filter segment 35, through the air space 38, through the lower filter segment 36, through the check valve 28, through the bore 12 of the lower tube 11, and into the mouth and lungs of the patient.

Since, as observed above, the path described in the immediately preceding paragraph is the most direct potential route for any contaminants associated with bodily fluids to pass between the care provider and the patient, the check valve 28 has been inserted to preclude the patient's exhaled breath from traveling from the lower tube 11 to the upper tube 3 Because the check valve 28 necessarily permits the exhaled breath of the care provider to pass from the upper tube 3 to the lower tube 11 in order to accomplish the desired resuscitation of the patient, the transmission filter 34 is so constructed as to minimize the possibility of fluids passing from the upper tube 3 to the lower tube 11, although the transmission filter 34 also impedes the travel of fluids from the lower tube 11 to the upper tube 3 in the event that any exhaled breath from the patient should manage to pass the check valve 28. The upper filter segment 35 is, therefore, preferably hydrophobic to repel any moisture in the breath from the care provider while the lower filter segment 36 is preferably hydrophilic to absorb any fluid that evades the upper filter segment 35 and enters the air space 38.

The air space 38, furthermore, creates a volume where fluids may accumulate without significantly obstructing the flow of the care provider's breath.

As mentioned above, the check valve 28 is preferably a duck-bill valve. And, preferably, the valve lips 39 axially extend into the bore 12 of lower tube 11 to maximize the possibility that most of the breath exhaled by the care giver will travel into lower tube 11 rather than escaping into the passage 31 and then through the apertures 25 into the atmosphere.

Figure 2:
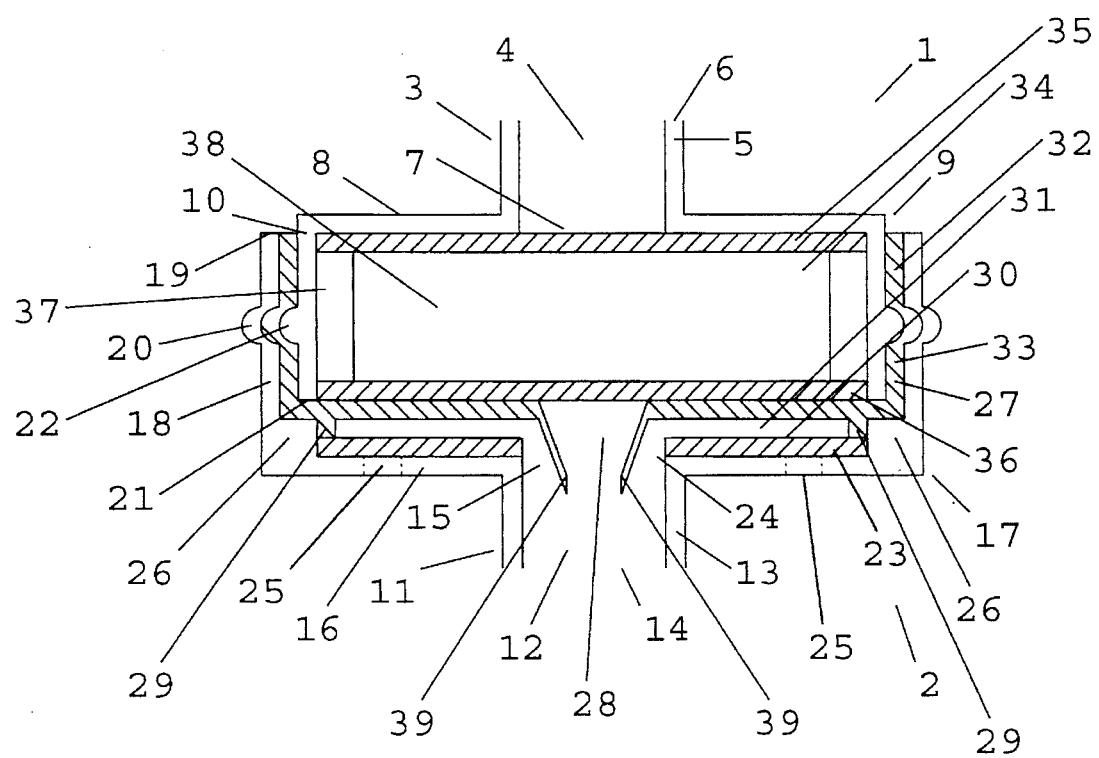
FIG. 2 portrays the Dual-filtered Rotary Isolation Valve with the valve lips open.

On the contrary, when the patient exhales, the exhaled breath from the patient will pass through the lower tube 11, into the passage 31, through the apertures 25, and into the atmosphere. If the care provider is not exhaling into the Dual-filtered Rotary Isolation Valve at the same time as the patient exhales, the valve lips 39 will remain closed so that the only route available to the patient's breath will be that course describe in the preceding sentence. If, however, the care provider exhales into the Dual-filtered Rotary Isolation Valve at the same time as the patient exhales, the valve lips 39 will open, as illustrated in FIG. 2, only if the breath from the care provider is stronger than the breath from the patient. In such a case, the patient's breath will still be able to follow the route described at the beginning of this paragraph and will not pass through the check valve 28 because of the stronger fluid dynamic force of the care provider's breath. With the valve lips 39 constructed so that such valve lips 39 cannot open wide enough to reach the tube wall 13 of the lower tube 11, it is improbable that breath of the care provider will be strong enough to force the patient's breath back into the patient's lungs.

Since the patient's breath is likely to reach the atmosphere, the exhalation filter 23 intercepts the patient's breath before such breath passes through the apertures 25. Preferably, the exhalation filter 23 is hydrophobic to repel any fluids within the breath of the patient.

The ability of the lower chamber segment 17 to rotate with respect to the upper chamber segment 9 will, when a mouthpiece (not shown) is attached to the first end 6 of the upper tube 3 and a mask is connected to the second end 15 of the lower tube 11, permit achieving the most comfortable and efficient orientation of the upper housing 1 with respect to the provider of care while simultaneously creating the most comfortable and efficient orientation of the lower housing 2 with respect to the patient. And, as mentioned previously, the extension of the diaphragm 27 into the space 33 between the wall 18 of the lower chamber segment 17 and the wall 10 of the upper chamber segment 9 permits the desired rotation while simultaneously creating an air-tight seal between the upper chamber segment 9 and the lower chamber segment 17 so that the patient's exhaled breath cannot escape through the space 33.

Figure 3:
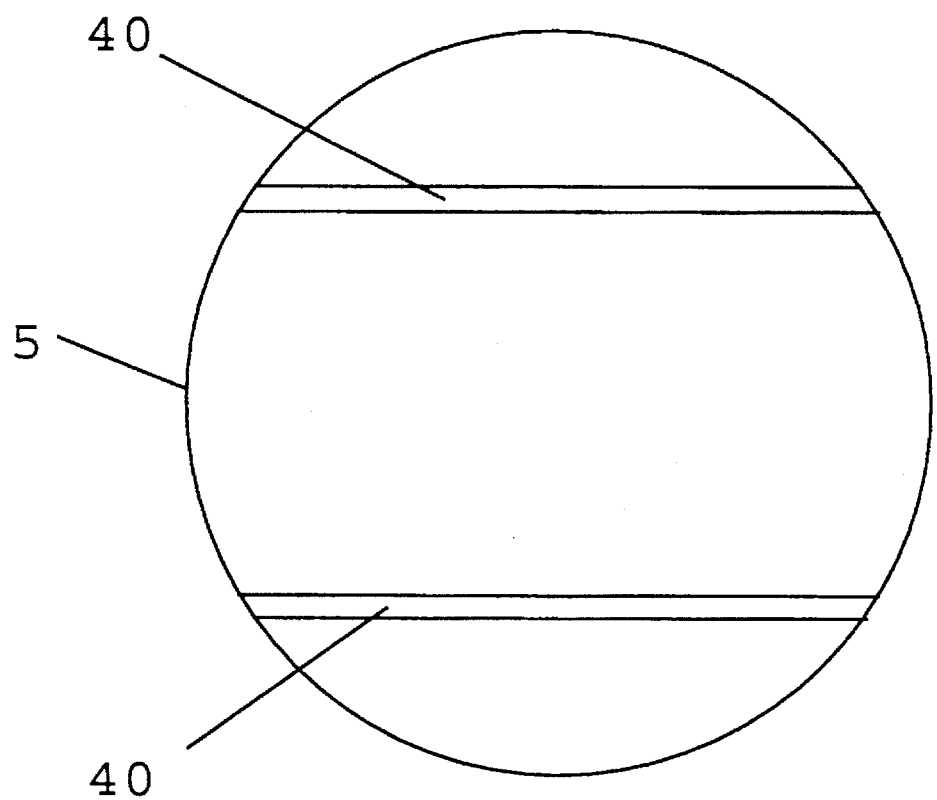
FIG. 3 shows the placement of the two thin bands across the second end of the upper tube in the Dual-filtered Rotary Isolation Valve.

Finally, as illustrated in FIG. 3, to preclude damage to the transmission filter 34 while minimizing the resistance to the flow of air through the upper tube 3, two thin bands 40 are preferably placed parallel to one another across the second end 7 of the upper tube 3 and connected to the tube wall 5 of the upper tube 3.

I claim:

1. A dual-filtered rotary isolation valve for resuscitation of patients, which comprises:

an upper housing having an upper tube containing a bore formed by a surrounding upper tube wall, the first end of which upper tube may either be placed directly into a care provider's mouth or be connected to a mouthpiece to be placed into the mouth of the care provider, the second end of which upper tube expands outward to create a top of an upper chamber segment and then returns to its original direction to from a wall of an upper chamber segment having a circular cross section concentrically located with respect to the cross section of the upper tube, the cross section of said upper tube also being circular, and the wall of the upper chamber segment protruding outward at a location between the top of the upper chamber segment and the bottom of the wall of the upper chamber to create annular ridge;

a lower housing having a lower tube with a containing a bore formed by a surrounding lower tube wall, the first end of which lower tube may either be placed directly into the patient's mouth or be connected to a mask to be placed around the nose and mouth of the patient or be attached to a mouthpiece to be inserted into the mouth of the patient, the second end of which lower tube expands outward to create a bottom of a lower chamber segment and then returns to its original direction to form a wall of a lower chamber segment having a circular cross section concentrically located with respect to the cross section of the lower tube, the cross section of said lower tube also being circular, the wall of the lower chamber segment bulging outward to create an annular channel at a location between the bottom of the lower chamber segment and the top of the wall of the lower chamber segment so aligned with the annular ridge in the wall of the upper chamber segment that the lower chamber segment can be snap-fit onto the upper chamber segment, the inner diameter of the wall of the lower chamber segment being slightly greater than the outer diameter of the wall of the upper chamber segment to permit the lower chamber argment to rotate with respect to the upper chamber segment, the inner diameter of the annular channel being slightly greater than the outer diameter of the annular ridge but not so much greater that the lower chamber segment could slip from the upper chamber segment once the lower chamber segment and the upper chamber segment have been snap-fit together, one or more apertures existing in the bottom of the lower chamber segment, and an annular step formed at the junction of the bottom of the lower chamber segment and the wall of the lower chamber segment;

an exhalation filter placed on the bottom of the lower chamber segment, which exhalation filter contains an aperture that is approximately aligned with the bore of the lower tube;

a flexible diaphragm having a check valve near the center of said flexible diaphragm, having a support which rests on the exhalation filter adjacent to the support but covering only the outer edge of the exhalation filter so that the majority of the surface of the exhalation filter that is opposite to the bottom of the lower chamber segment is adjacent a passage which communicates with the bore of the lower tube, and having an outer edge that extends into the space between the wall of the lower chamber segment and the wall of the upper chamber segment with the bottom of the wall of the upper chamber segment resting on the diaphragm to create an air-tight seal between the upper chamber segment and the lower chamber segment; and a transmission filter fills the upper chamber segment and is adjacent to the diaphragm.

2. The dual-filtered rotary isolation valve for resuscitation of patients as recited in claim 1, wherein:

the transmission filter has an upper filter segment and a lower filter segment, the upper filter segment being adjacent to the top of the upper chamber segment and the lower filter segment being adjacent to the diaphragm, with an annular spacer separating the upper filter segment from the lower filter segment and thereby creating an air space.

3. The dual-filtered rotary isolation valve for resuscitation of patients as recited in claim 2, wherein:

the upper filter segment is hydrophobic.

4. The dual-filtered rotary isolation valve for resuscitation of patients as recited in claim 3, wherein:

the lower filter segment is hydrophilic.

5. The dual-filtered rotary isolation valve for resuscitation of patients as recited in claim 4, wherein:

the exhalation filter is hydrophobic.

6. The dual-filtered rotary isolation valve for resuscitation of patients as recited in claim 5, further comprising:

two thin bands placed parallel to one another across the second end of the upper tube and connected to the tube wall of the upper tube.

7. The dual-filtered rotary isolation valve for resuscitation of patients as recited in claim 1, wherein:

the check valve is a duck-bill valve, the valve lips of which duck-bill valve axially extend into the bore of the lower tube.

8. The dual-filtered rotary isolation valve for resuscitation of patients as recited in claim 7, wherein:

the transmission filter has an upper filter segment and a lower filter segment, the upper filter segment being adjacent to the top of the upper chamber segment and the lower filter segment being adjacent to the diaphragm, with an annular spacer separating the upper filter segment from the lower filter segment and thereby creating an air space.

9. The dual-filtered rotary isolation valve for resuscitation of patients as recited in claim 8, wherein:

the upper filter segment is hydrophobic.

10. The dual-filtered rotary isolation valve for resuscitation of patients as recited in claim 9, wherein:

the lower filter segment is hydrophilic.

11. The dual-filtered rotary isolation valve for resuscitation of patients as recited in claim 10, wherein:

the exhalation filter is hydrophobic.

12. The dual-filtered rotary isolation valve for resuscitation of patients as recited in claim 11, further comprising:

two thin bands placed parallel to one another across the second end of the upper tube and connected to the tube wall of the upper tube.

* * * * *